US00PP36953P2

(12) United States Plant Patent
De Wet et al.

(10) Patent No.: US PP36,953 P2
(45) Date of Patent: Sep. 9, 2025

(54) ***SALVIA* PLANT NAMED 'DWSahyb03'**

(50) Latin Name: *Salvia coccinea*
Varietal Denomination: DWSahyb03

(71) Applicants: Charles Andrew De Wet, Gauteng (ZA); Quinton Bean, Gauteng (ZA)

(72) Inventors: Charles Andrew De Wet, Gauteng (ZA); Quinton Bean, Gauteng (ZA)

(73) Assignee: De Wet Plant Breeders Pty. Ltd., Gauteng (ZA)

( * ) Notice: Subject to any disclaimer, the term of this patent is extended or adjusted under 35 U.S.C. 154(b) by 0 days.

(21) Appl. No.: 18/755,624

(22) Filed: Jun. 26, 2024

(51) Int. Cl.
*A01H 5/02* (2018.01)
*A01H 6/50* (2018.01)

(52) U.S. Cl.
USPC ..... Plt./475

(58) Field of Classification Search
USPC ..... Plt./475
CPC ... A01H 5/02; A01H 5/12; A01H 5/00; A01H 6/508; A01H 6/50
See application file for complete search history.

(56) References Cited

PUBLICATIONS

Greenhouse Grower, Readers Choice Annuals Vote for your favorite among this year's new annual introductions, retrieved on Apr. 23, 2025 at https://www.greenhousegrower.com/readerschoice/readers-choice-annuals/, 16 pp. (Year: 2025).*
Proven Winners Unplugged Red scarlet sage, retrieved on Apr. 23, 2025 at https://www.provenwinners.com/plants/salvia/unplugged-red-scarlet-sage-salvia-coccinea, 4 pp. (Year: 2025).*

* cited by examiner

*Primary Examiner* — June Hwu
(74) *Attorney, Agent, or Firm* — C. Anne Whealy

(57) ABSTRACT

A new and distinct cultivar of *Salvia* plant named 'DWSahyb03', characterized by its mostly upright to somewhat outwardly spreading plant habit; vigorous growth habit and rapid growth rate; freely branching habit; dense and bushy appearance; dark green-colored leaves; freely flowering habit; long and erect inflorescences with numerous bright red-colored flowers; and excellent container and garden performance.

2 Drawing Sheets

Figure 1:
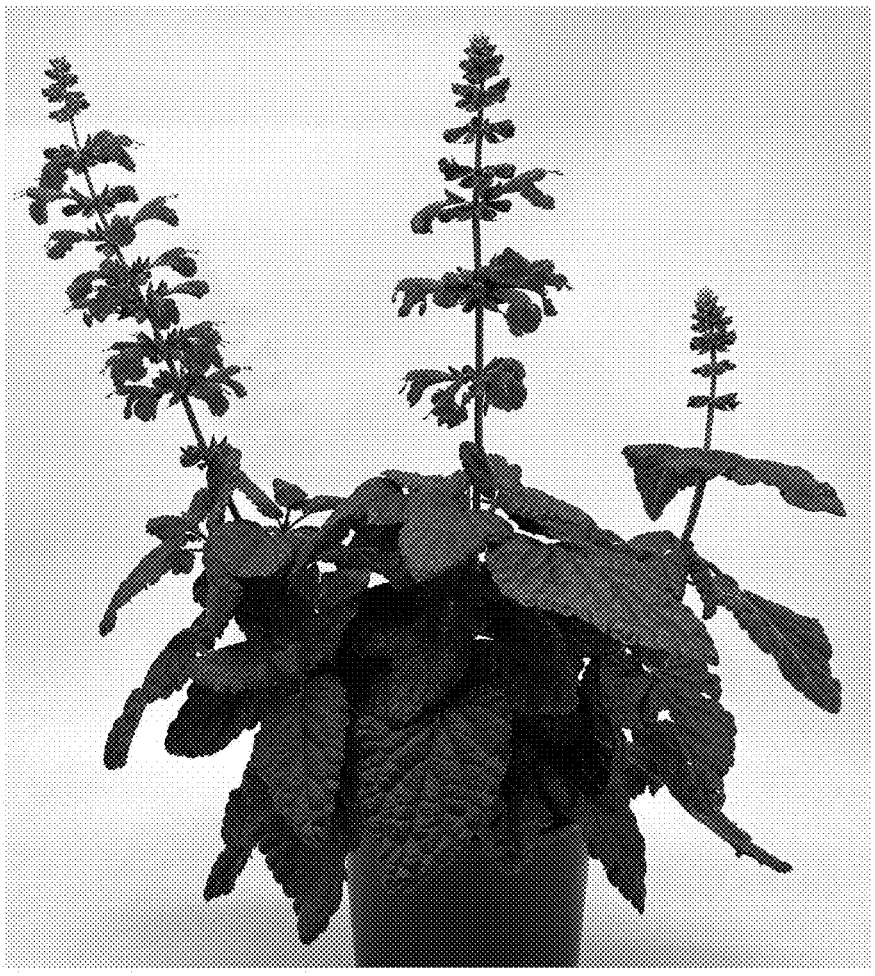

Botanical designation: *Salvia coccinea.*
Cultivar denomination: 'DWSahyb03'.

BACKGROUND OF THE INVENTION

The present invention relates to a new and distinct cultivar of *Salvia* plant, botanically known as *Salvia coccinea* and hereinafter referred to by the name 'DWSahyb03'.

The new *Salvia* plant is a naturally-occurring whole plant mutation of *Salvia coccinea* 'Forest Fire', not patented. The new *Salvia* plant was discovered and selected by the Inventors as a single flowering plant from within a population of plants of 'Forest Fire' in a controlled greenhouse environment in Sandton, Gauteng, South Africa in July 2016.

Asexual reproduction of the new *Salvia* plant by vegetative terminal cuttings in Sandton, Gauteng, South Africa since February 2017 has shown that the unique features of this new *Salvia* plant are stable and reproduced true to type in successive generations.

SUMMARY OF THE INVENTION

Plants of the new *Salvia* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'DWSahyb03'. These characteristics in combination distinguish 'DWSahyb03' as a new and distinct *Salvia* plant:

1. Mostly upright to somewhat outwardly spreading plant habit.
2. Vigorous growth habit and rapid growth rate.
3. Freely branching habit; dense and bushy appearance.
4. Dark green-colored leaves.
5. Freely flowering habit.
6. Long and erect inflorescences with numerous bright red-colored flowers.
7. Excellent container and garden performance.

Plants of the new *Salvia* can be compared to plants of the mutation parent, 'Forest Fire'. Plants of the new *Salvia* differ primarily from plants of 'Forest Fire' in the following characteristics:

1. Plants of the new *Salvia* are more compact than plants of 'Forest Fire'.
2. Plants of the new *Salvia* have shorter internodes than plants of 'Forest Fire'.
3. Plants of the new *Salvia* have thicker leaves than plants of 'Forest Fire'.
4. Plants of the new *Salvia* have larger flowers than plants of 'Forest Fire'.

Plants of the new *Salvia* can be compared to plants of *Salvia coccinea* 'Lady in Red', not patented. In side-by-side comparisons, plants of the new *Salvia* differ from plants of 'Lady in Red' in the following characteristics:

1. Plants of the new *Salvia* are more compact than plants of 'Lady in Red'.
2. Plants of the new *Salvia* have shorter internodes than plants of 'Lady in Red'.
3. Plants of the new *Salvia* have thicker leaves than plants of 'Lady in Red'.
4. Plants of the new *Salvia* have larger flowers than plants of 'Lady in Red'.

Plants of the new *Salvia* can also be compared to plants of *Salvia coccinea* 'Yucatan', not patented. In side-by-side comparisons, plants of the new *Salvia* differ from plants of 'Yucatan' in the following characteristics:

1. Plants of the new *Salvia* are more compact than plants of 'Yucatan'.
2. Plants of the new *Salvia* have shorter internodes than plants of 'Yucatan'.
3. Plants of the new *Salvia* have thicker leaves than plants of 'Yucatan'.
4. Plants of the new *Salvia* have larger flowers than plants of 'Yucatan'.

BRIEF DESCRIPTION OF THE PHOTOGRAPHS

The accompanying colored photographs illustrate the overall appearance of the new *Salvia* plant showing the colors as true as it is reasonably possible to obtain in colored reproductions of this type. Colors in the photographs may differ slightly from the color values cited in the detailed botanical description which accurately describe the colors of the new *Salvia* plant.

The photograph on the first sheet (FIG. 1) is a side perspective view of a typical flowering plant of 'DWSahyb03' grown in a container.

Figure 2:
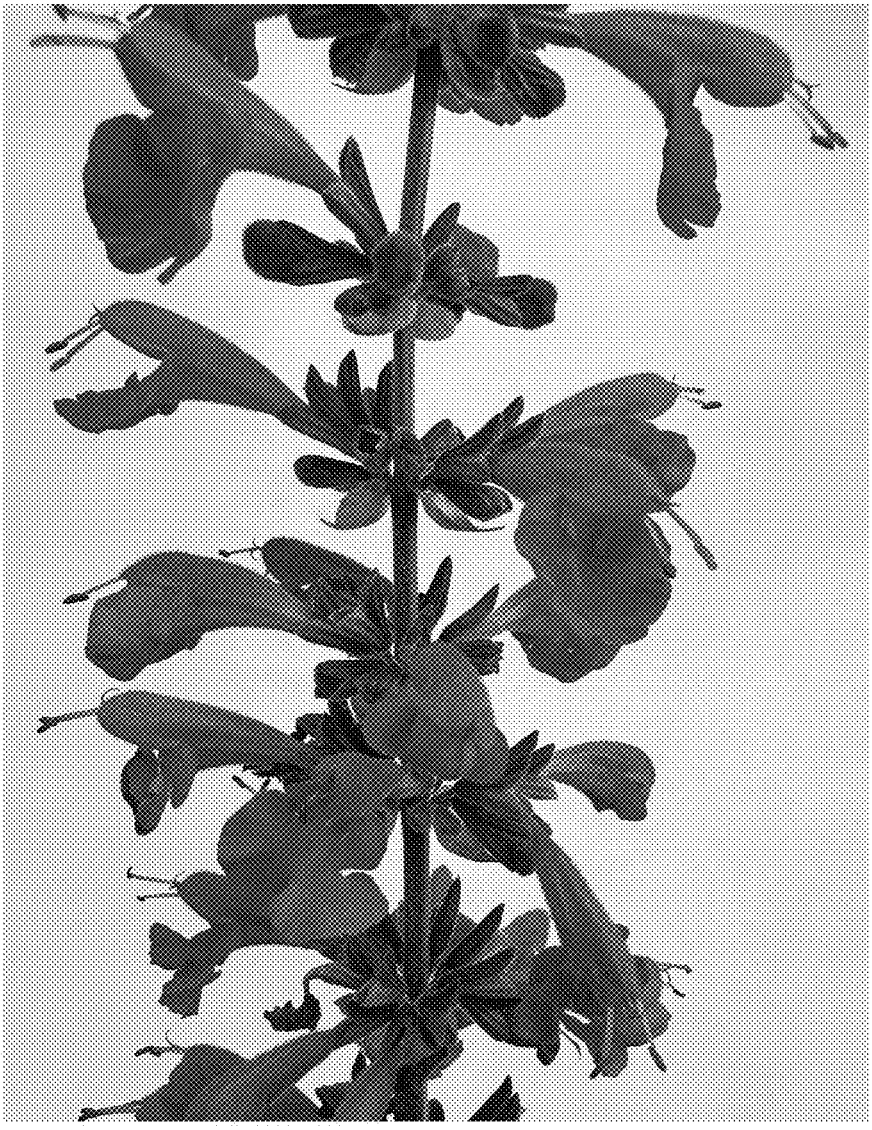

The photograph on the second sheet (FIG. 2) is a close-up view of a typical inflorescence of 'DWSahyb03'.

DETAILED BOTANICAL DESCRIPTION

The aforementioned photographs and following observations and measurements describe plants grown during the late winter and early spring in 10.75-cm containers in a glass-covered greenhouse in Loudon, New Hampshire and under cultural practices typical of commercial *Salvia* production. During the production of the plants, day and night temperatures averaged 20° C. Plants were eight weeks from planting rooted cuttings when the photographs and description were taken. In the following description, color references are made to The Royal Horticultural Society Colour Chart, 2015 Edition, except where general terms of ordinary dictionary significance are used.

Botanical classification: *Salvia coccinea* 'DWSahyb03'.

Parentage: Naturally-occurring whole plant mutation of *Salvia coccinea* 'Forest Fire', not patented.

Propagation:

*Type*.—By vegetative terminal cuttings.

*Time to initiate roots, summer*.—About five to seven days at temperatures ranging from about 21° C. to 24° C.

*Time to initiate roots, winter*.—About seven to nine days at temperatures ranging from about 18° C. to 21° C.

*Time to produce a rooted young plant from unrooted cuttings, summer*.—About four weeks at temperatures ranging from about 24° C. to 27° C.

*Time to produce a rooted young plant from unrooted cuttings, winter*.—About five weeks at temperatures ranging from about 18° C. to 21° C.

*Root description*.—Fine, fibrous; typically white in color, actual color of the roots is dependent on substrate composition, water quality, fertilizer type and formulation, substrate temperature and physiological age of roots.

*Rooting habit*.—Freely branching; medium density.

Plant description:

*Plant and growth habit*.—Herbaceous perennial typically grown as a container and garden plant; mostly upright to somewhat outwardly spreading plant habit; vigorous growth habit and rapid growth rate.

*Branching habit*.—Freely basal branching with about three to five primary lateral branches with two secondary lateral branches potentially developing at every node; bushy and dense appearance.

*Plant height*.—About 34 cm to 46 cm.

*Plant width*.—About 28 cm to 37 cm.

*Lateral branch description*.—Length: About 22 cm to 26 cm. Diameter, at the base: About 7 mm to 8 mm. Internode length: Variable, about 3 cm to 4 cm. Strength: Strong, sturdy, flexible; not brittle. Aspect: Initially upright then somewhat outwardly spreading. Texture and luster: Densely pubescent; pubescence, fine; longitudinally ridged; semi-glossy. Color, developing: Close to 146A. Color, developed: Close to 146A variably overlain with close to between 83A and 86A.

Leaf description:

*Arrangement*.—Opposite, simple.

*Length*.—About 9 cm to 11.5 cm.

*Width*.—About 7 cm to 8 cm.

*Shape*.—Broadly ovate.

*Apex*.—Broadly acute.

*Base*.—Auriculate.

*Margin*.—Moderately crenate; slightly undulate.

*Texture and luster, upper surface*.—Slightly to moderately pubescent; velvety; glossy.

*Texture and luster, lower surface*.—Mostly glabrous with dense pubescence along veins; slightly glossy.

*Venation pattern*.—Pinnate, reticulate.

*Color*.—Developing leaves, upper surface: Close to 147A. Developing leaves, lower surface: Close to 147B. Fully expanded leaves, upper surface: Close to between 147A and 139A; midvein, proximally, close to between 144A and 146A, and distally, close to between 147A and 139A; lateral venation, close to between 147A and 139A. Fully expanded leaves, lower surface: Close to 147B; venation, close to 144B to 144C.

*Petioles*.—Length: About 4.2 cm to 4.5 cm. Diameter: About 2 mm to 2.5 mm. Strength: Strong; flexible. Texture and luster, upper and lower surfaces: Densely pubescent; pubescence, fine; glossy. Color, upper and lower surfaces: Close to 144A.

Flower description:

*Flower arrangement and shape*.—Single bilabiate flowers arranged on erect terminal and axillary racemes; freely flowering habit with about six to eight flowers per alternate clusters, at least 24 clusters per inflorescence and about 144 to 192 flowers developing per inflorescence; flowers face mostly outwardly.

*Fragrance*.—None detected.

*Natural flowering season*.—Early flowering habit; depending on temperature, plants begin flowering about six to seven weeks after planting rooted young plants; plants flower from late spring until frost in the garden in New Hampshire.

*Flower longevity*.—Depending on temperature, flowers last about five to seven days on the plant; flowers persistent.

*Inflorescence buds*.—Length: About 1.25 cm to 1.5 cm. Diameter: About 7.5 mm to 8 mm. Shape: Conical. Texture and luster: Pubescent; slightly glossy. Color: Close to between 144A and 146A.

*Inflorescence height*.—About 20 cm to 23 cm.

*Inflorescence diameter*.—About 6 cm to 7 cm.

*Flower buds*.—Length: About 7.5 mm to 8 mm. Diameter: About 3.5 mm to 4 mm. Shape: Narrowly obovate. Texture and luster: Pubescent; slightly glossy. Color: Close to 146A.

*Flower diameter*.—About 1.5 cm to 1.75 cm.

*Flower length*.—About 2.8 cm to 3.2 cm.

*Flower throat diameter*.—About 5 mm.

*Flower tube length*.—About 1.5 cm to 1.7 cm.

*Flower tube diameter, proximally*.—About 1.5 mm to 2 mm.

*Petals*.—Arrangement: Bi-labiate petals fused forming an upper galea and three lower petals fused forming a broader lower protruding lip. Upper galea: Length: About 1 cm. Width: About 5 mm. Shape: Cordate; overall shape, hood-like. Apex: Cordate with a single deep emargination. Base: Fused. Margin: Entire; not undulate. Texture and luster, upper surface: Densely pubescent; slightly glossy. Texture and luster, lower surface: Smooth, glabrous; matte. Color: When developing and fully developed, upper surface: Close to 45A. When developing and fully developed, lower surface: Close to 45C. Lower lip: Length: About 1.5 cm to 1.7 cm. Width: About 1.1 cm to 1.4 cm. Shape: Spatulate with cordate tendencies. Apex: Cordate with a single deep emargination. Base: Fused. Margin: Entire; slightly undulate. Texture and luster, upper and lower surfaces: Smooth, glabrous; slightly iridescent; matte. Color: When developing and fully developed, upper surface: Close to N45A. When developing and fully developed, lower surface: Close to 45C. Throat, texture and luster: Smooth, glabrous; slightly glossy. Throat color: Close to 49D. Tube, texture and luster: Smooth, glabrous; slightly glossy. Tube color: Proximally, close to NN155D, and distally, close to 49A to 49B.

*Calyx*.—Arrangement: Single whorl of two sepals fused towards the base into a tubular calyx. Calyx length: About 1 cm. Calyx diameter: About 3 mm. Sepal length: About 1 cm. Sepal width: About 4 mm. Sepal shape: Linear. Sepal apex: Sharply acute. Sepal margin: Free part, entire. Sepal texture and luster, inner surface: Smooth, glabrous; slightly glossy. Sepal texture and luster, outer surface: Pubescent; slightly glossy. Color: When developing and fully developed, inner surface: Close to between 144A and 146A. When developing and fully developed, outer surface: Close to 146A; apex tinged with close to between 83A and 86A.

*Peduncles*.—Length: About 18 cm to 28 cm. Diameter: About 3 mm to 4 mm. Strength: Strong, flexible. Aspect: Mostly erect. Texture and luster: Densely pubescent; pubescence, fine; somewhat glossy. Color: Close to 146A variably overlain with close to between 83A and 86A.

*Pedicels*.—Length: About 3.5 mm. Diameter: About 1 mm. Strength: Strong, flexible. Aspect: About 45° from peduncle axis. Texture and luster: Moderately to densely pubescent; somewhat glossy. Color: Close to 146A.

*Reproductive organs*.—Stamens: Quantity per flower: Two. Filament length: About 1.2 cm. Filament color: Proximally, close to 62C, and distally, close to N57A. Anther size: About 0.75 mm by 2 mm. Anther shape: Narrowly oblong. Anther color: Close to N144A. Pollen amount: None observed. Pistils: Quantity per flower: One. Pistil length: About 2.6 cm. Style length: About 2.5 cm. Style color: Proximally, close to N57A, and distally, close to 62C. Stigma length: About 1.5 mm. Stigma shape: Bipartite; narrowly linear; reflexed. Stigma color: Close to N57A. Ovary color: Close to 154D.

*Seeds and fruits*.—To date, seed and fruit production has not been observed on plants of the new *Salvia*.

Pathogen & pest resistance: To date, plants of the new *Salvia* have not been noted to be resistant to pathogens and pests common to *Salvia* plants.

Garden performance: Plants of the new *Salvia* have exhibited good garden performance and to be tolerant to rain, wind and temperatures from about 2° C. to 40° C.

It is claimed:

1. A new and distinct *Salvia* plant named 'DWSahyb03' as herein illustrated and described.

* * * * *